United States Patent

Masumoto et al.

[11] Patent Number: 5,954,501
[45] Date of Patent: Sep. 21, 1999

[54] ORTHODONTIC APPLIANCE

[75] Inventors: Tsuyoshi Masumoto; Akihisa Inoue; Tao Zhang, all of Sendai; Mikio Mottate, Okuma-machi; Kikuo Nishi, Haramachi, all of Japan

[73] Assignee: GAC International, Inc., Central Islip, N.Y.

[21] Appl. No.: 08/422,393

[22] Filed: Apr. 14, 1995

[30] Foreign Application Priority Data

Apr. 25, 1994 [JP] Japan ................................ 6-107372

[51] Int. Cl.$^6$ ............................................. A61C 3/00
[52] U.S. Cl. ................................................. 433/8; 433/9
[58] Field of Search ............................ 433/8, 9, 20

[56] References Cited

U.S. PATENT DOCUMENTS

| | | | |
|---|---|---|---|
| 4,197,643 | 4/1980 | Burstone et al. | 433/20 |
| 5,088,923 | 2/1992 | Andreiko | 433/9 |
| 5,232,361 | 8/1993 | Sachdeva et al. | 433/8 |
| 5,252,066 | 10/1993 | Fairhurst | 433/8 |
| 5,267,854 | 12/1993 | Schmitt | 433/8 |

FOREIGN PATENT DOCUMENTS

| | | |
|---|---|---|
| 0 433 670 A1 | 6/1991 | European Pat. Off. . |
| 0 494 688 A1 | 7/1992 | European Pat. Off. . |
| 0 622 067 A1 | 11/1994 | European Pat. Off. . |
| 54079996 | 6/1979 | Japan . |
| A-07062502 | 3/1995 | Japan . |

*Primary Examiner*—Nicholas D. Lucchesi
*Attorney, Agent, or Firm*—Kenyon & Kenyon

[57] ABSTRACT

Orthodontic appliances in accordance with the present invention are formed from amorphous alloys having a supercooling liquid region. The appliances have high corrosion resistance, high durability and high strength. The appliances are particularly useful when changes and adjustments in the orthodontic state become necessary in the course of orthodontic treatment. The present invention also provides improvements in the base surfaces of orthodontic appliances adapted to be bonded to tooth surfaces. The appliances can consequently be securely affixed to tooth surfaces.

27 Claims, 10 Drawing Sheets

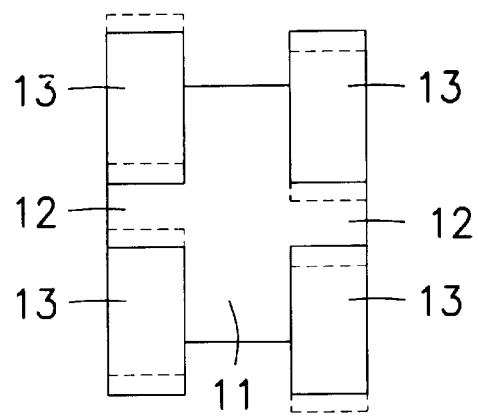 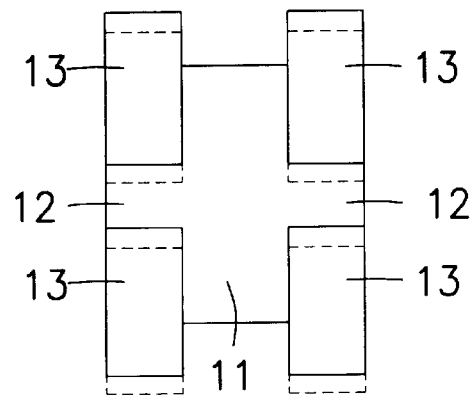
Fig. 10A    Fig. 10B
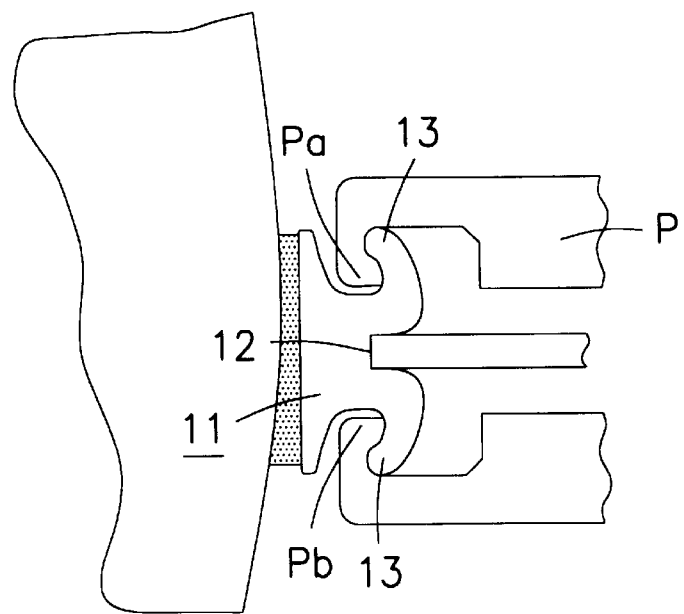
Fig. 11

ORTHODONTIC APPLIANCE

TECHNICAL FIELD OF THE INVENTION

The present invention relates to orthodontic appliances such as brackets, buccal tubes and bands used for orthodontic treatment as well as other auxiliary orthodontic products.

BACKGROUND INFORMATION

Brackets designed to retain arch wires will be used as examples to describe the material composition and characteristics of prior art orthodontic appliances. Brackets are ordinarily formed of stainless steel, titanium, ceramic or plastic materials. Brackets made of stainless steel generally have superior strength characteristics and can be more easily manufactured than other brackets. However, the presence of chromium and nickel in the stainless steel has been known to cause allergic reactions in some patients.

Alloyed titanium brackets have superior corrosion resistance properties. Pure titanium brackets generally lack sufficient strength for orthodontic use. The Ti-6Al-4V titanium alloy has sufficient strength, but includes a toxic vanadium element. Moreover, the presence of this alloy inside a patient's mouth with other metals may cause a galvanic cell effect with the risk of metal elution. In addition, the alloy is expensive and not well suited to manufacturing processes.

Ceramic brackets have an aesthetically pleasing appearance, but because they are harder than tooth enamel, they may cause tooth surfaces to become scratched during chewing. In addition, tooth enamel may be damaged when ceramic brackets are removed from tooth surfaces during or after completion of orthodontic treatment due to the stiffness of the material. Also, a practitioner may be forced to grind tooth surfaces with a diamond tool to remove any portions of ceramic brackets remaining on the tooth surfaces.

Plastic brackets also have an aesthetically pleasing appearance. Plastic brackets however do not have substantial mechanical strength and may break or deform when external forces are applied to the bracket by arch wires during treatment. Also, plastic brackets have relatively high rates of water absorption and tend to discolor easily from food colorants. Moreover, there is substantial frictional resistance to smooth movement of arch wires relative to plastic brackets, which may lengthen the period of orthodontic treatment.

With these prior brackets, when changes and adjustments are required during orthodontic treatment, ordinarily either the arch wires are removed from the brackets, bent, and reinstalled to continue orthodontic treatment, or the brackets are removed from the tooth surfaces and reattached in desired positions. Thus, a substantial amount of work is required by a practitioner during orthodontic treatment.

The drawbacks of prior art brackets are also applicable at least to some degree to other orthodontic appliances.

SUMMARY OF THE INVENTION

The present invention comprises an orthodontic appliance formed from an amorphous alloy having a supercooling liquid region. Accordingly, the orthodontic appliance includes the amorphous alloy properties of high corrosion resistance, durability and sufficient strength, thereby overcoming material related problems of prior orthodontic appliances.

With the use of an amorphous alloy having a supercooling liquid region, orthodontic appliances can be adjusted by applying a relatively low force to the appliance after heating it to a prescribed temperature. Accordingly, any necessary changes and adjustments in the orthodontic state can be quickly and easily made even in the course of orthodontic treatment. Specifically, use of an amorphous alloy with a supercooling liquid region over 20K and an amorphous alloy proportion of over 30% permits particularly easy adjustment of the orthodontic appliance.

The alloy composition is an amorphous alloy having the general formula $X_a$—$Y_b$—$M_c$, where X may be one or more metals selected from among Zr, Ti and Hf in the IVb column of the Periodic Table, Y may be one or more metals selected from among Al, Zr, Hf, Ti and rare earth metals, and M may be one or more transition metals selected from among Fe, Co, Ni and Cu, and where a=50 to 80, b=5 to 20 and c=0 to 50.

The base elements, Zr, Ti and Hf, are suitable for use in orthodontic appliances because they are not harmful to the human body. The M elements, Fe, Co, Ni and Cu, in the presence of Zr, Ti and Hf, increase the amorphic formability of the material.

Examples of preferred alloy compositions include:

(1) $Zr_{63}$—$Al_{12}$—$Co_3$—$Ni_7$—$Cu_{15}$
(2) $Zr_{60}$—$Al_{15}$—$Co_5$—$Ni_{15}$—$Cu_5$
(3) $Zr_{65}$—$Al_{7.5}$—$Cu_{27.5}$
(4) $Zr_{55}$—$Al_{20}$—$Co_{20}$
(5) $Zr_{70}$—$Al_{15}$—$Fe_{15}$
(6) $Zr_{60}$—$Al_{15}$—$Ni_{25}$

BRIEF DESCRIPTION OF THE DRAWINGS

FIGS. 10(A) and 10(B) are front views illustrating bracket deformation adjustment.

FIG. 11 is a side view of an orthodontic bracket illustrating one method of bracket heating.

DETAILED DESCRIPTION

Figure 1:
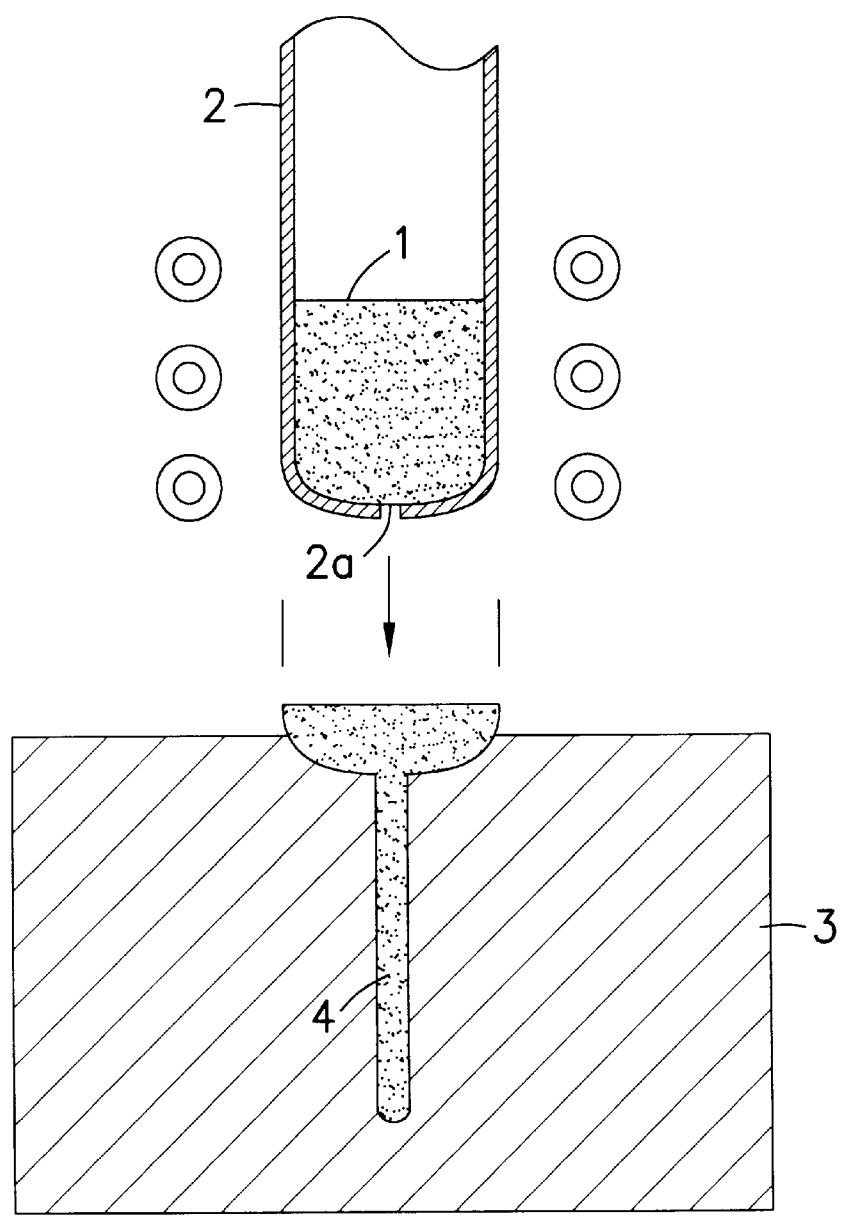
FIG. 1 is a cross-section view of an apparatus for forming bulk material samples.

The mother alloy 1 of each of the respective example alloy compositions (1) to (6) set forth above is introduced into a quartz nozzle 2 shown in FIG. 1 having small hole 2a with a diameter of φ1.0 to 2.0 mm. The material is then melted by induction heating under vacuum. The quartz nozzle 2 is then lowered towards a copper mold 3, and pressurized argon gas is applied to eject the liquid from the hole 2a into the copper mold 3. The material is then quenched at a cooling speed of $10^4$ to $10^7$ K/s to form bulk material pieces 4 in sizes of φ3.0×50 mm. The mother alloy is formerly melted in an arc melting furnace to remove gas from the porous Zr metal, followed by the addition and dissolving of the other elements therein.

Figure 2:
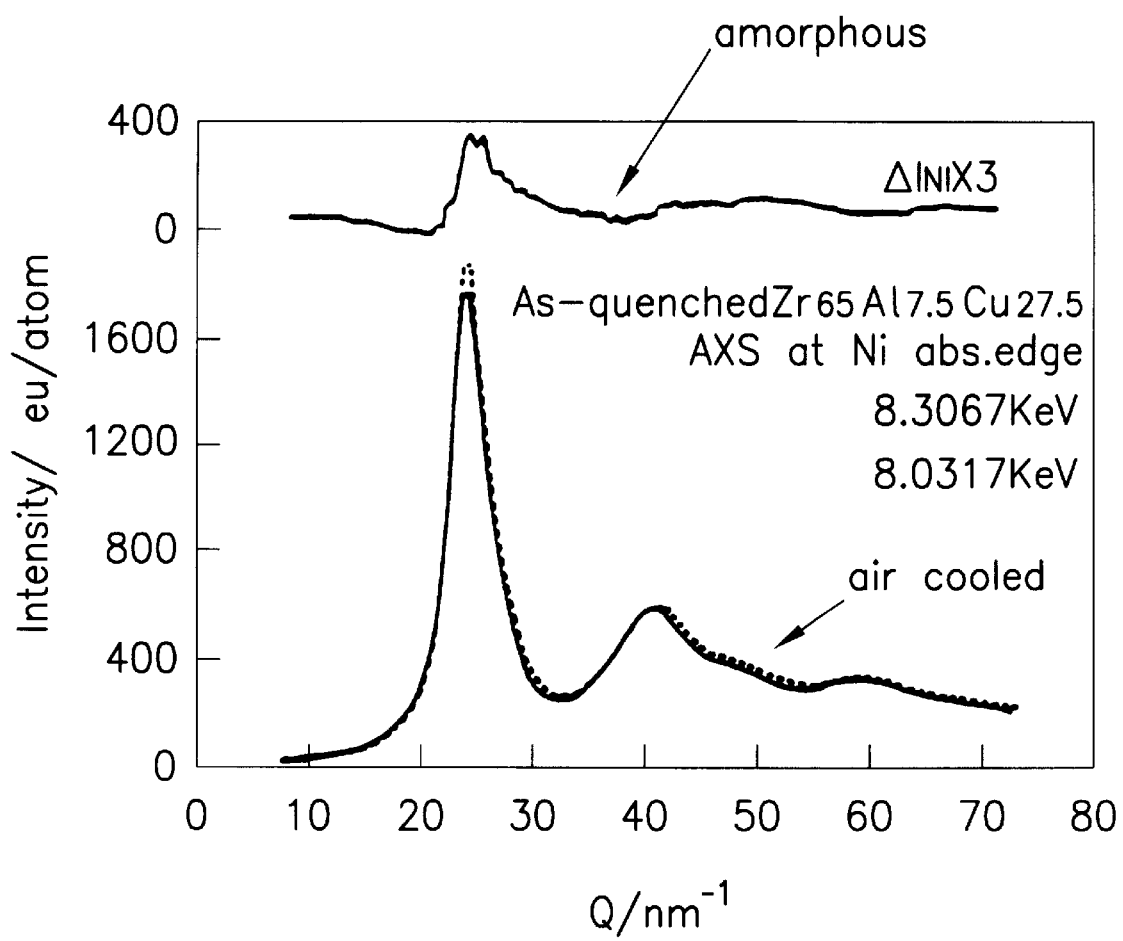
FIG. 2 is a graph illustrating the diffraction results from an X-ray diffraction apparatus.

Structural analysis was performed on an X-ray diffraction apparatus to determine whether an amorphous alloy had been formed. The air cooled products showed a distinct Zr presence as shown in FIG. 2. However, the bulk material 4 from alloy composition (3) did not show a clear peak in the Kα line region of Zr.

The amorphous alloys preferably have an amorphous metal content of over 30%.

Figure 3:
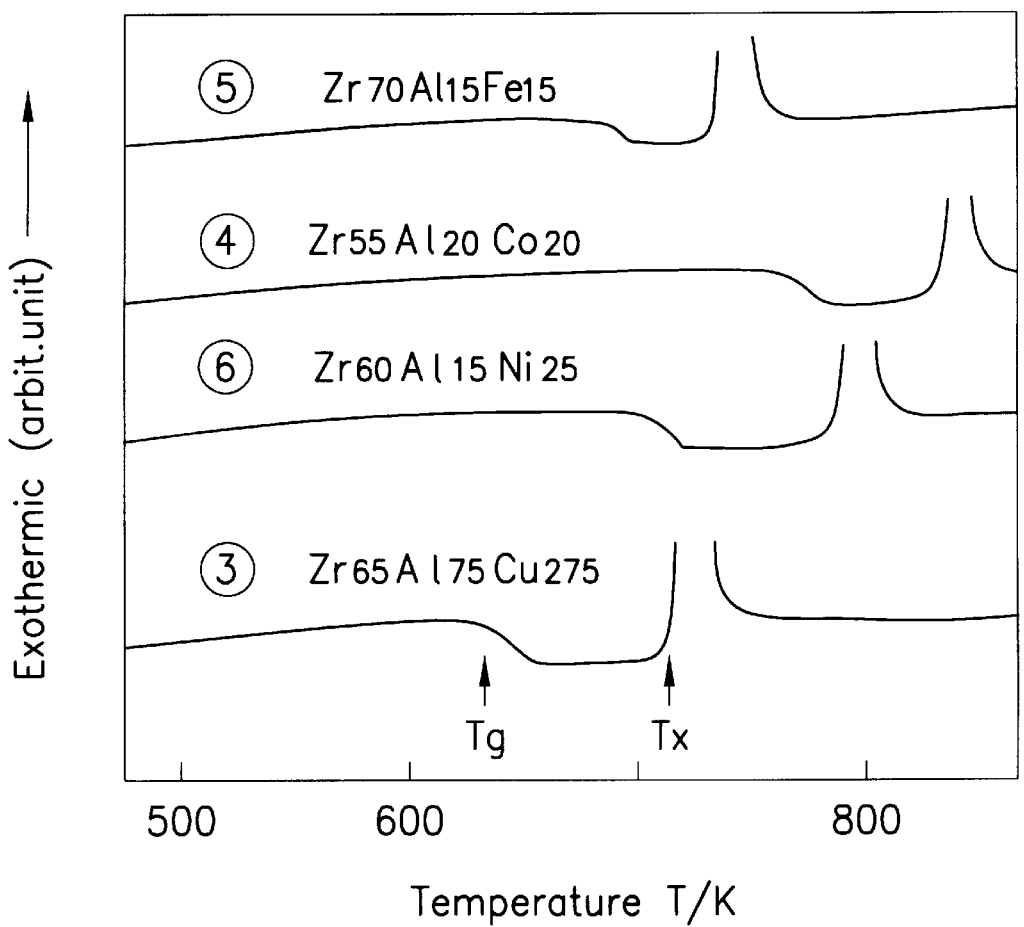
FIG. 3 is a graph illustrating the results of differential scanning calorimeter diffraction analysis.

Differential scanning calorimeter diffraction (DSC curves) analysis were also performed on the amorphous alloys to investigate their heat properties. The results shown in FIG. 3 indicate significant differences in the glass transition temperatures Tg and the crystallization temperatures Tx of the individual alloy compositions. The maximum values for the supercooling liquid region ΔTx (Tx−Tg) are 56K for alloy composition (5) containing Fe, 69K for alloy composition (4) containing Co, 77K for alloy composition (6) containing Ni, and 88K for alloy composition (3) containing Cu.

As shown, the amorphous alloy of alloy composition (3) containing Cu has the widest supercooling liquid region ΔTx, and the Tg and Tx defining the supercooling liquid region ΔTx are in the low temperature zone of 630 to 710K.

Figure 4:
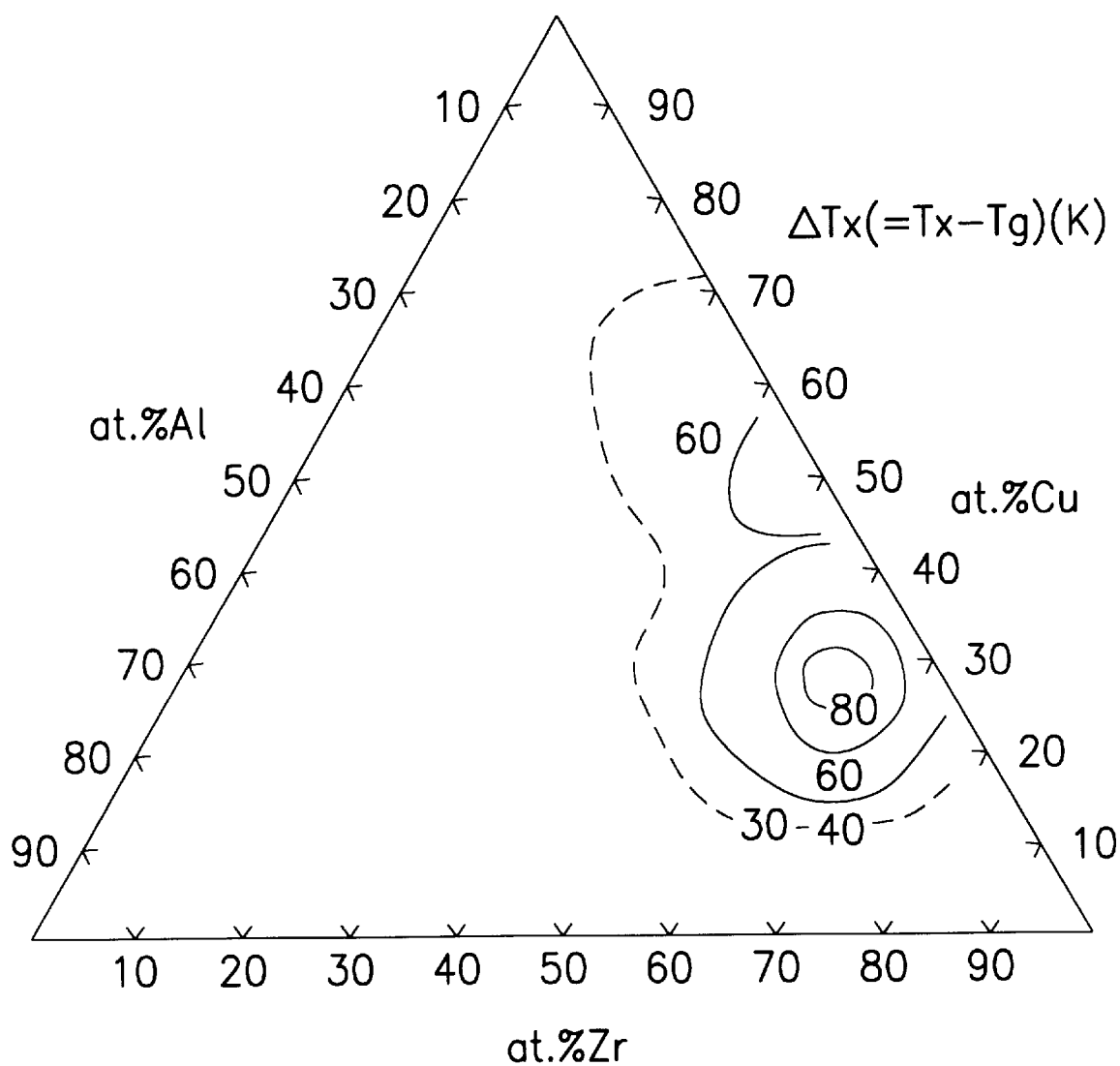
FIG. 4 is a graph illustrating the compositional dependence of the supercooling liquid region on ternary structure.

FIG. 4 illustrates the relationship between the elemental proportions and the supercooling liquid region ΔTx of alloy composition (3). The alloy composition shown in the diagram has a range of 59 to 77% Zr, 5 to 13% Al and 25 to 32% Cu. The alloy composition (3) of $Zr_{65}$—$Al_{7.5}$—$Cu_{27.5}$ provides the highest supercooling liquid region ΔTx of 80K. Although not illustrated, the highest supercooling liquid region ΔTx for alloy compositions (1) and (2) was 100K and 90K, respectively.

Figure 5:
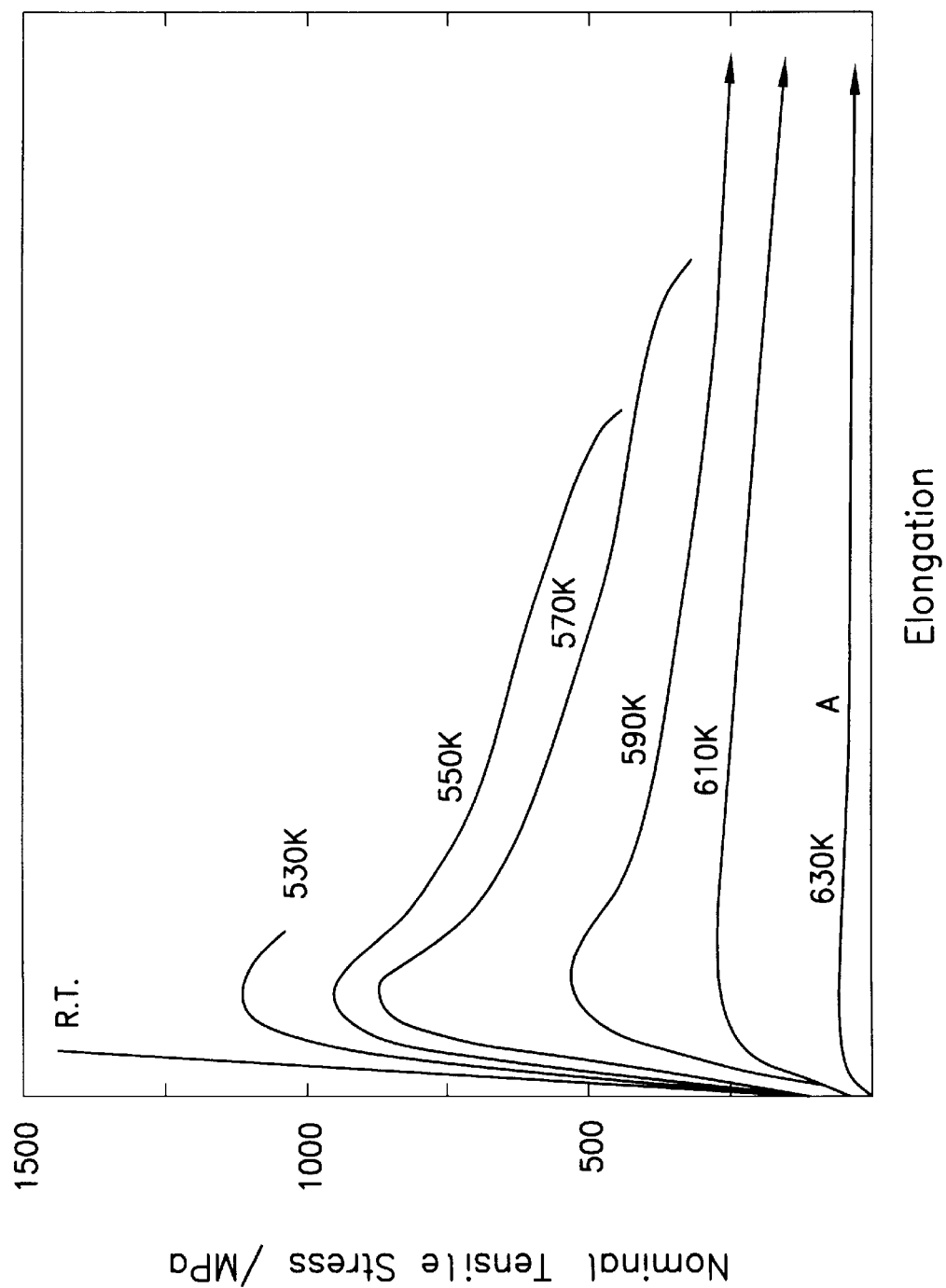
FIG. 5 is a graph illustrating stress-strain curves relative to temperature changes.

FIG. 5 shows stress-strain curves relative to temperature changes in the Tg vicinity preceding the supercooling liquid region ΔTx of amorphous alloy composition (3). At "A" where Tg exceeds 630K, strain is produced from very little stress. This indicates superplasticity phenomena at the supercooling liquid region ΔTx. Also, at 570K and 600K just preceding Tg, deformation occurs with relatively substantial stress, after which stress is reduced and deformation occurs continuously.

Alloy compositions (1) and (2) having Co, Ni and Cu instead of $Cu_{27.5}$ of composition (3) showed generally the same results when the differential scanning calorimeter diffractions (DSC curves) and stress-strain curves were analyzed.

The amorphous alloys of alloy compositions (1) and (2) at room temperature and at body temperature (37° C.) had a Vickers hardness of Hv 400 and tensile strength of 1,200 MP. This strength is significantly higher than that of the precipitation hardened type stainless steel and the Ti—6Al—4V alloy in present use, making the amorphous alloy compositions particularly suitable for orthodontic appliances.

An example of a bracket formed from an amorphous alloy having the above-mentioned properties is described below.

Figure 6:
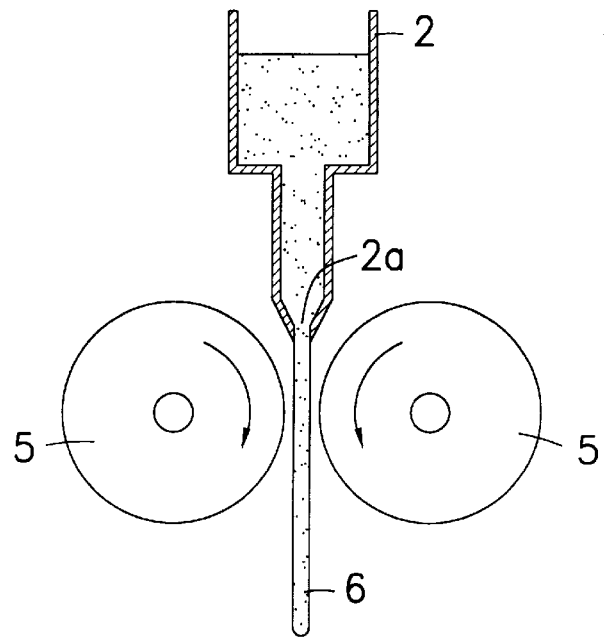
FIG. 6 is a cross-section view of an apparatus for manufacturing continuous wire.
Figure 7A:
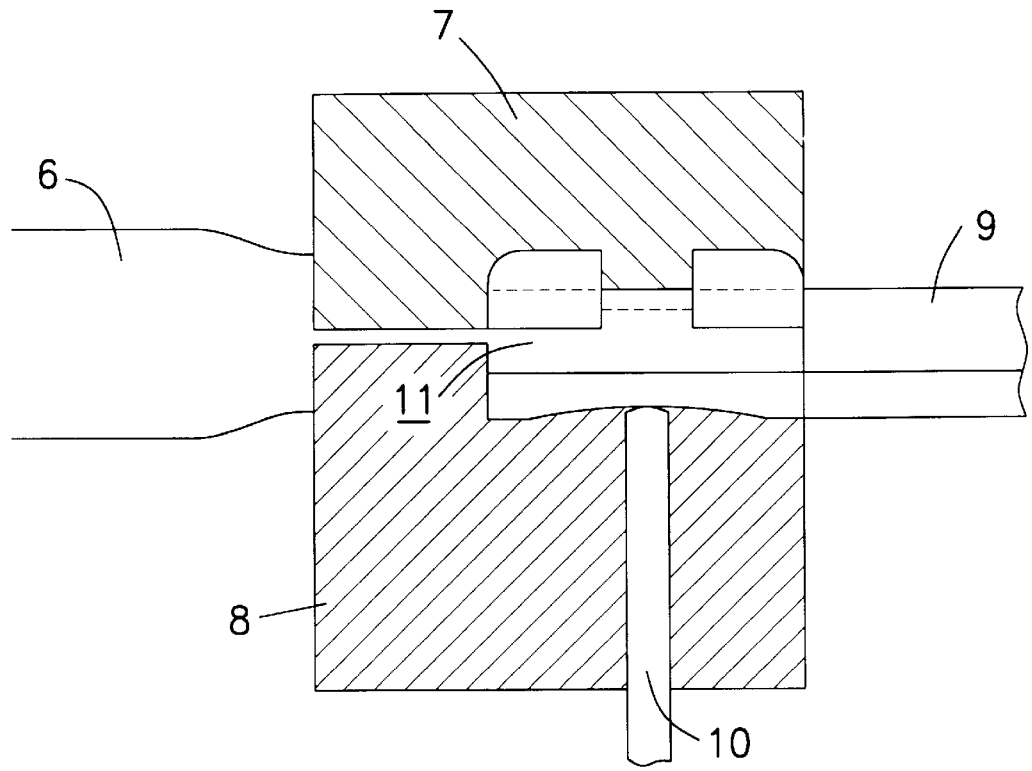
FIGS. 7(A) and 7(B) are front and side cross-section views, respectively, of a hot working press for forming brackets from continuous wire.
Figure 7B:
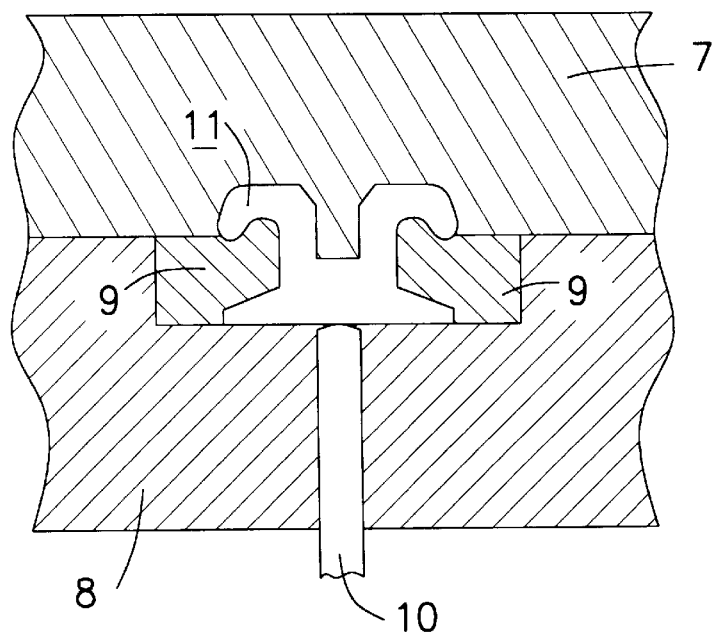

As shown in FIG. 6, fused material is ejected from a small hole 2a of a nozzle 2 to a groove between a pair of rotating steel rollers 5 to form a continuous amorphous wire 6 having a 3.0 mm diameter. Then, as shown in FIG. 7(A) and 7(B), the continuous wire 6 is introduced in a hot working press comprising an upper mold portion 7, a lower mold portion 8, a slide mold portion 9, and an ejector pin 10. The tip portion of the wire 6 is heated to 670K before insertion in the press mold. When the wire is pressed under a strain speed ($5.0×10^{-3}$/S) corresponding to the viscoelastic behavior of the supercooling liquid region, a bracket 11 is formed corresponding to the shape of the mold cavity.

A bracket 11 formed by such a method has the high corrosion resistance, high durability and sufficient strength characteristics of amorphous alloys. Furthermore, the bracket is formed from amorphous alloys that are safe for use in the human body. The bracket also has a wide supercooling liquid region, and can consequently be deformed for adjustment as needed both before and during orthodontic treatment.

Figure 8:
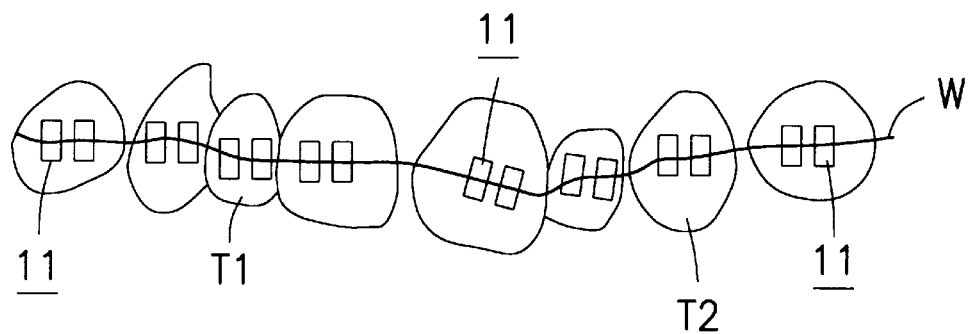
FIG. 8 is a front view of a dental arch illustrating the orthodontic state at the start of treatment.
Figure 9:
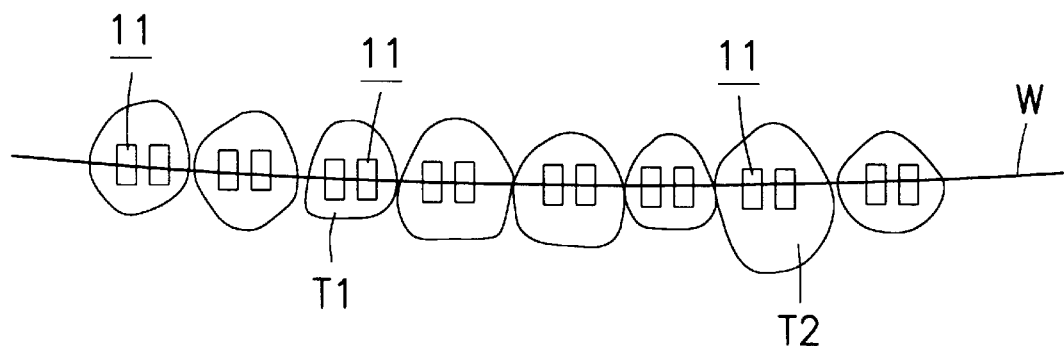
FIG. 9 is a front view of a dental arch illustrating the orthodontic state after completion of treatment.

FIG. 8 illustrates a possible orthodontic state of a dental arch at the start of orthodontic treatment. After 6 months of treatment, this state may be corrected to that shown in FIG. 9. In the latter state, the arch wire W is nearly straight. However, because of the initial bracket positioning, tooth T1 is tilted in the mesial direction and tooth T2 is displaced in the occlusal direction. With prior art orthodontic brackets, further orthodontic treatment would require either the removal of the arch wire W from the brackets 11 and further bending of the arch wire as required, or the removal of the brackets 11 from the tooth surfaces and reattachment of the brackets in proper positions on the tooth surfaces.

In accordance with the present invention, however, the slots of the brackets 11 can be easily adjusted by heating the brackets to a relatively low temperature of about 570–600K and applying a relatively weak force thereto.

For example, in bracket 11 attached to the tooth T1, an angled slot can be formed by moving slot 12 on the distal side of the bracket upwardly and slot 12 on the mesial side downwardly as shown in FIG. 10A. In bracket 11 attached to tooth T2, both slots 12 retaining arch wire W may be moved in an occlusal (downward) direction as shown in FIG. 10B. The brackets can thus be easily adjusted while on the patient's teeth, and are an improvement over prior brackets that require removal and reattachment of the bracket or removal and bending of the arch wire.

The bracket 11 may be electrically heated to temperatures of 570 to 600K by applying low voltage direct current to the bracket using pliers containing electrodes. As shown in FIG. 11, the sides of the bracket can be clasped under wings 13 with the positive and negative electrode tips Pa and Pb, respectively, of pliers P while current is passed therethrough.

Figure 12:
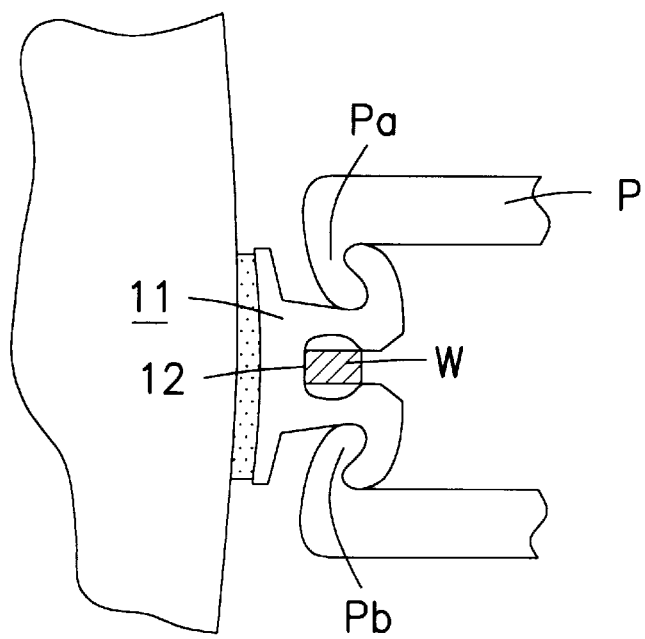
FIG. 12 is a side view of an orthodontic bracket illustrating deformation adjustment with an arch wire attached to the bracket.

When performing retention near the end of orthodontic treatment, the slot 12 may be closed about the arch wire W by a similar heating and deforming process with pliers P having electrodes attached thereto as shown in FIG. 12.

Figure 13:
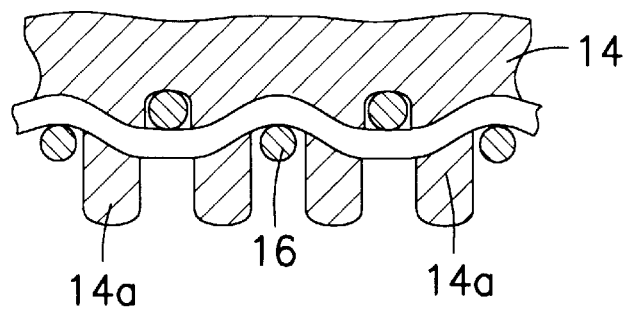
FIG. 13 is an enlarged cross-section view of a portion of the base surface of a bracket illustrating a method of forming an undercut on the base surface.

Because amorphous alloys are chemically inert, it may be difficult to securely bond the brackets to tooth surfaces using conventional dental adhesives. To improve bracket adhesion, undercuts may be formed in the base surface 14 of the bracket as shown in FIG. 13 by extruding the amorphous alloy through the interstices of a mesh 16, which may be made of steel for example, in a heated atmosphere of about 570 to 600K. The tips of the resulting extruded columnar projections are then slightly flattened. The extruded surface can then be cooled and washed with a strong acid like ferric chloride or hydrofluoric acid.

Figure 14A:
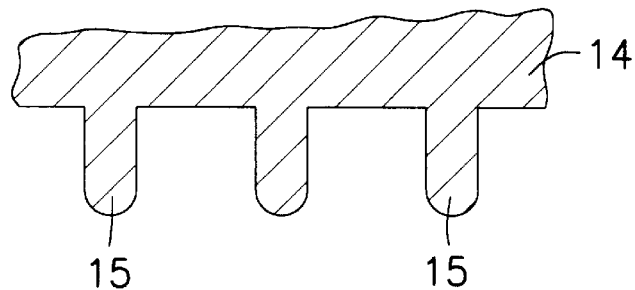
FIGS. 14(A) and 14(B) are enlarged cross-section views of portions of the base surface of brackets illustrating undercuts formed by alternate means.
Figure 14B:
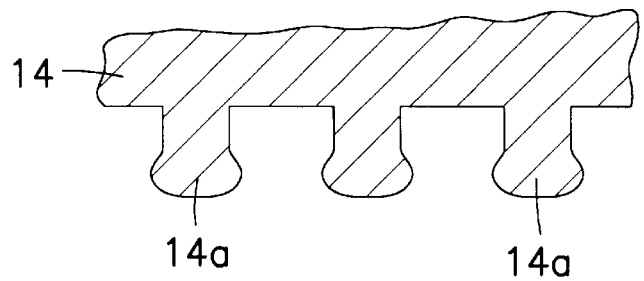

It is also possible to form undercuts 14a shown in FIG. 14 by forming a plurality of projections 15 in the bracket base surface 14 in a metal mold and then slightly flattening the tips of the projections 15 in a heated atmosphere.

While the above examples illustrate adjustable orthodontic brackets 11, a variety of other adjustable orthodontic appliances including buccal tubes, bands, and arch wires can be similarly formed.

Although brackets 11 in the above examples were formed from continuous wire comprising bulk materials, the brackets, buccal tubes or other appliances may alternatively be made by forming a powder of the above material, mixing the powder with a binder, forming the appliance by means of metal injection molding, debinding, sintering in a furnace, and then rapid cooling.

In summary, orthodontic appliances of the present invention are formed from amorphous alloys having a supercooling liquid region. The appliances have high corrosion resistance, high durability and high pliable strength. The appliances are particularly useful when changes and adjustments in the orthodontic state become necessary in the course of orthodontic treatment.

The present invention also provides improvements in the base surfaces of orthodontic appliances adapted to be bonded to tooth surfaces. The appliances can consequently be securely affixed to tooth surfaces.

We claim:

1. An orthodontic appliance comprising an amorphous alloy having a supercooling liquid region greater than 20K and including an amorphous alloy content of over 30%.

2. The orthodontic appliance of claim 1, wherein the appliance comprises an amorphous alloy having the general formula $X_a$—$Y_b$—$M_c$, wherein X is one or more metals selected from the group consisting of Zr, Ti, Hf, Mg and rare earth metals, Y is one or more metals selected from the group consisting of Al, Zr, Hf, Ti and rare earth metals, and M is one or more metals selected from the group consisting of Fe, Co, Ni and Cu, and wherein a=50 to 80, b=5 to 20 and c=0 to 50.

3. The orthodontic appliance of claim 1, wherein the appliance comprises $Zr_{63}$—$Al_{12}$—$Co_3$—$Ni_7$—$Cu_{15}$.

4. The orthodontic appliance of claim 1, wherein the appliance comprises $Zr_{60}$—$Al_{15}$—$Co_5$—$Ni_{15}$—$Cu_5$.

5. The orthodontic appliance of claim 1, wherein the appliance comprises $Zr_{65}$—$Al_{7.5}$—$Cu_{27.5}$.

6. The orthodontic appliance of claim 1, wherein the appliance comprises $Zr_{55}$—$Al_{20}$—$Co_{20}$.

7. The orthodontic appliance of claim 1, wherein the appliance comprises $Zr_{70}$—$Al_{15}$—$Fe_{15}$.

8. The orthodontic appliance of claim 1, wherein the appliance comprises $Zr_{60}$—$Al_{15}$—$Ni_{25}$.

9. The orthodontic appliance of claim 1, wherein the appliance comprises a base surface adapted to be affixed to a tooth surface, and wherein the base surface includes undercuts thereon to facilitate secure bonding thereof to the tooth surface.

10. The orthodontic appliance of claim 9, wherein said undercuts on said base surface define a plurality of projections.

11. The orthodontic appliance of claim 10, wherein said projections include flattened tips.

12. An orthodontic appliance comprising an amorphous alloy having a supercooling liquid region and having the general formula $X_a$—$Y_b$—$M_c$, wherein X is one or more metals selected from the group consisting of Zr, Ti, Hf, Mg and rare earth metals, Y is one or more metals selected from the group consisting of Al, Zr, Hf, Ti and rare earth metals, and M is one or more metals selected from the group consisting of Fe, Co, Ni and Cu, and wherein a=50 to 80, b=5 to 20 and c=0 to 50.

13. The orthodontic appliance of claim 12, wherein the supercooling liquid region is greater than 20K.

14. The orthodontic appliance of claim 12, wherein the appliance includes an amorphous alloy content of over 30%.

15. The orthodontic appliance of claim 12, wherein the appliance comprises $Zr_{63}$—$Al_{12}$—$Co_3$—$Ni_7$—$Cu_{15}$.

16. The orthodontic appliance of claim 12, wherein the appliance comprises $Zr_{60}$—$Al_{15}$—$Co_5$—$Ni_{15}$—$Cu_5$.

17. The orthodontic appliance of claim 12, wherein the appliance comprises $Zr_{65}$—$Al_{7.5}$—$Cu_{27.5}$.

18. The orthodontic appliance of claim 12, wherein the appliance comprises $Zr_{55}$—$Al_{20}$—$Co_{20}$.

19. The orthodontic appliance of claim 12, wherein the appliance comprises $Zr_{70}$—$Al_{15}$—$Fe_{15}$.

20. The orthodontic appliance of claim 12, wherein the appliance comprises $Zr_{60}$—$Al_{15}$—$Ni_{25}$.

21. The orthodontic appliance of claim 12, wherein the appliance comprises a base surface adapted to be affixed to a tooth surface, and wherein the base surface includes undercuts thereon to facilitate secure bonding thereof to the tooth surface.

22. The orthodontic appliance of claim 12, wherein said undercuts on said base surface define a plurality of projections.

23. The orthodontic appliance of claim 22, wherein said projections include flattened tips.

24. An orthodontic appliance comprising an amorphous alloy having a supercooling liquid region, wherein the appliance includes a base surface adapted to be affixed to a tooth surface, and wherein the base surface includes undercuts thereon to facilitate secure bonding thereof to the tooth surface.

25. The orthodontic appliance of claim 24, wherein said undercuts on said base surface define a plurality of projections.

26. The orthodontic appliance of claim 24, wherein said projections include flattened tips.

27. The orthodontic appliance of claim 24, wherein the appliance comprises an amorphous alloy having the general formula $X_a$—$Y_b$—$M_c$, wherein X is one or more metals selected from the group consisting of Zr, Ti, Hf, Mg and rare earth metals, Y is one or more metals selected from the group consisting of Al, Zr, Hf, Ti and rare earth metals, and M is one or more metals selected from the group consisting of Fe, Co, Ni and Cu, and wherein a=50 to 80, b=5 to 20 and c=0 to 50.

* * * * *